United States Patent [19]
Schroeppel

[11] Patent Number: 5,755,764
[45] Date of Patent: May 26, 1998

[54] IMPLANTABLE CARDIAC STIMULATION CATHETER

[75] Inventor: Edward A. Schroeppel, Lake Jackson, Tex.

[73] Assignee: Sulzer Intermedics Inc., Angleton, Tex.

[21] Appl. No.: 710,049

[22] Filed: Sep. 10, 1996

[51] Int. Cl.$^6$ ........................................ A61N 1/05
[52] U.S. Cl. ................................ 607/122; 607/127
[58] Field of Search ............................. 607/119, 122, 607/126, 127, 131

[56] References Cited

U.S. PATENT DOCUMENTS

| | | |
|---|---|---|
| 3,416,534 | 12/1968 | Quinn. |
| 4,146,036 | 3/1979 | Dutcher et al. ........................ 607/127 |
| 4,481,953 | 11/1984 | Gold et al. ........................... 607/122 |
| 4,830,006 | 5/1989 | Haluska et al. . |
| 4,922,927 | 5/1990 | Fine et al. . |
| 5,040,534 | 8/1991 | Mann et al. . |
| 5,044,375 | 9/1991 | Bach, Jr. et al. . |
| 5,050,601 | 9/1991 | Kupersmith et al. . |
| 5,090,422 | 2/1992 | Dahl et al. . |
| 5,111,811 | 5/1992 | Smits ................................... 607/127 |
| 5,115,818 | 5/1992 | Holleman et al. . |
| 5,129,394 | 7/1992 | Mehra . |
| 5,174,288 | 12/1992 | Bardy et al. ............................ 607/2 |
| 5,230,337 | 7/1993 | Dahl et al. . |
| 5,342,414 | 8/1994 | Mehra ................................. 128/642 |
| 5,374,287 | 12/1994 | Rubin ................................. 607/122 |
| 5,476,502 | 12/1995 | Rubin ................................. 607/127 |
| 5,522,872 | 6/1996 | Hoff ................................... 607/119 |
| 5,545,183 | 8/1996 | Altman ................................ 607/5 |

*Primary Examiner*—William E. Kamm
*Assistant Examiner*—George R. Evanisko
*Attorney, Agent, or Firm*—John R. Merkling; Conley, Rose & Tayon

[57] ABSTRACT

An implantable cardiac stimulation catheter includes a helical electrode segment disposed about a central core of electrically non-conductive material for delivering an electrical pulse to the heart of the patient. The catheter may include a tubular electrode segment disposed on the catheter and electrically connected with the helical electrode. The helical and tubular electrode segments may be defibrillation electrode segments. The catheter may also include a demand pacer electrode for delivering a demand pacing pulse to the heart and/or a fixation mechanism for securing the catheter within the patient's heart.

11 Claims, 4 Drawing Sheets

IMPLANTABLE CARDIAC STIMULATION CATHETER

BACKGROUND OF THE INVENTION

1. Field of the Invention

The present invention relates generally to implantable cardiac stimulation devices and systems for regulating the contraction of a heart. More particularity, the invention relates to a defibrillation and demand pacer catheter, and more particularly to a defibrillation electrode arrangement.

2. Description of the Related Art

Implantable medical devices for treating irregular contractions of the heart with electrical stimuli are well known in the art. Some of the most common forms of such implantable devices are defibrillators and pacemakers.

Defibrillators are implantable medical devices used to treat fibrillation, a condition characterized by rapid, chaotic electrical and mechanical activity of the heart's excitable myocardial tissue that results in an instantaneous cessation of blood flow from the heart. Defibrillation is a technique employed to terminate fibrillation by applying one or more high energy electrical pulses to the heart in an effort to overwhelm the chaotic contractions of individual tissue sections and to restore the normal synchronized contraction of the total mass of tissue.

A pacemaker, or pacer, is an implantable medical device that delivers low energy electrical pulses to stimulate a patient's heart to beat at a desired rate in instances where the heart itself is incapable of proper self-regulation. This occurs when the heart's natural pacemaker, which causes the rhythmic electrical excitation of the heart and pumping of blood, malfunctions due to age or disease. Demand pacing is a process used to maintain normal beating of a heart having this condition.

Various types of defibrillators and demand pacers have been suggested in the prior art. For example, large electrical patches sewn to the exterior surface of the heart have been used to deliver defibrillation pulses to the heart. Implantation of such patch electrodes requires opening of the patient's chest during thoracic surgery. For demand pacing, pulses may be applied to the heart with the use of a demand pacer catheter having an exposed metal surface, or demand pacer electrode, extending through a vein and into the heart.

Those involved in the medical arts recognized that prior art defibrillators required a high threshold level of energy for effective defibrillation, which limited the useful life-span of the devices and, more significantly, posed a significant risk of causing electrolysis of the blood and myocardial damage. It was realized that the defibrillation electrode configuration played an important role in the amount of energy needed to achieve successful defibrillation. This led to the development of transvenous defibrillation leads having long coil-shaped defibrillation electrodes for implantation into the right ventricle of the heart through a vein. For example, U.S. Pat. No. 4,922,927, the entire disclosure of which is incorporated herein by reference, discloses a defibrillation electrode made up of a plurality of separate wires wound side-by-side to form a tight coil. The coil was disposed upon an insulated tubular member and had a length sufficient to extend throughout the entire length of the ventricular chamber to provide sufficient electrode surface area for defibrillation.

Transvenous cardiac stimulation leads, such as the device of U.S. Pat. No. 4,922,927, were configured to also carry a demand pacing electrode. Thus, a single device implantable in one surgical procedure could provide defibrillation and demad pacing pulses for heart patients suffering from both irregular heart beat and, at times, cardiac fibrillation. This eliminated the need for multiple and complex surgical procedures to attach the prior art electrodes required for both types of treatments.

Another defibrillation electrode configuration for use with dual purpose transvenous catheters is disclosed in U.S. Pat. Nos. 5,476,502 and 5,374,287 to Rubin, which are also incorporated herein by reference in their entireties. The "Rubin" catheter included either a helical or lance shaped defibrillation electrode for delivering a defibrillation pulse directly to the interior of the septum of the patient's heart. The length of the helix-shaped electrode to be screwed into the septum from the right ventricle, about 0.5 cm to 1.0 cm, was substantially shorter than the conventional coiled transvenous defibrillation electrodes.

It is believed that the helix shaped defibrillation electrode of U.S. Pat. Nos. 5,476,502 and 5,374,287 achieved effective defibrillation at a lower energy threshold, decreasing the risk of electrolysis, or burning of the heart tissue, and improving the useful life of the electrode. At the same time, however, the Rubin catheter was difficult to navigate through the contours of the vein and heart during insertion and removal because of the sharp frontal protraction of the helix or lance. Further, the risk of tearing or puncturing the soft tissue of the vein and heart was great, and such result could cause serious damage. Additionally, exposure of the grooves and cavities of the helix or the protraction of the lance when positioned in the right ventricle of the heart could increase the risk of blood clots or thrombi formation thereabouts, which could lead to serious injury, such as stroke, if a clot broke away from the electrode and became lodged in a blood vessel.

Additional problems were presented by the procedure that was required to drive and thereby implant the helix or lance into the heart. Because of the soft tissue structure of the heart, it is often difficult to screw an object of the proposed size of the helix into the heart. Further, the sheer force of attempting to screw the helix, or propel the lance, into the heart could cause serious trauma and damage to the heart tissue. Finally, the act of affixing the electrode to the septum as suggested would risk puncturing the septum (the wall separating the right and left ventricles of the heart) which, likewise, poses a risk of serious injury.

Thus, there exists a need for a catheter capable of providing both low threshold defibrillation and effective demand pacing that does not heighten the risk of damage to the heart or venous tissue and injury to the patient. It should be noted that due to the nature of the subject medical conditions and treatment relating thereto, including the implantation and use of defibrillators and pacemakers, no device can be risk free or prevent injury; however, it is believed that catheters for use therefor can be designed to better protect against injury caused by implantation. Accordingly, there is a need for a catheter that could be implanted and removed with relative ease and a reduced risk of puncturing or tearing the venous and heart tissue. Such a catheter would be especially well received if it could be implanted with relative ease and without having to be driven or screwed into the heart, thereby reducing the risk of damaging the heart during surgical implantation of the medical device. Ideally, the outer surface of the defibrillation electrode would have no cavities or hollow interior cores, which the prior art has shown promote the formation of blood clots, or thrombi, in the heart. Preferably, the new device could otherwise employ known and reliable components, such as electrical conductors, optional fixation mechanisms, electrical power supplies and circuitry.

SUMMARY OF THE INVENTION

In accordance with the present invention, there is provided an implantable catheter having a helical electrode segment disposed about a central core of electrically nonconductive material. The electrode is connected to an elongated, flexible, electrically non-conductive probe and is supplied with electrical power for delivering electrical pulses to the heart from a first electrical condutor that extends through the probe and is associated with a power source.

An electrically non-conductive material forms the central core of the helical electrode segment. The core may consist of a separate plug, or the electrode may be disposed over the distal end of the probe. In one embodiment of the invention the plug, or probe, is constructed of polyurethane, and in another instance of silicone rubber. Other materials that prove to be compatible for use with the invention may likewise be utilized. The helical electrode segment thus provides the known benefit of the helix shape as an effective low threshold defibrillation electrode, while allowing implantation and removal of the catheter without the heightened risk of catching on, tearing or otherwise damaging the vein or heart. Because the electrode does not have any sharp protrusions, it cannot be screwed or driven into the heart, which could cause serious injury.

A tubular electrode segment may be electrically coupled with the helicial electrode segment and disposed on the probe. Providing two such defibrillation electrode segments allows greater flexibility in achieving the optimal surface area for electrical transmission of low threshold defibrillation, and permits the sizing of each electrode segment to accommodate longitudinal flexibility of the catheter. In the present preferred embodiment of the invention, the optimal total surface area of the defibrillation electrode segments is between about 1.2 cm$^2$ to about 2.0 cm$^2$. The electrode segments, however, can be sized as desired to achieve effective and efficient cardiac stimulation and flexibility.

Depending upon the desired application for the catheter, the invention may also be used as a demand pacer and, thus, include any of a variety of demand pacer electrodes and sensors that are presently available or may become available. Such devices, if used, would be disposed upon the probe, insulated from the defibrillator electrode segments and electrically connected with a second electrical conductor that extends through the probe and provides electrical power to the demand pacer electrode. The catheter may also include a ground electrode disposed upon the probe a distance from the other electrodes to receive the pulses delivered to the heart tissue and transmit them back through a third electrical conductor extending through the probe.

The invention may also be adapted for fixation of the distal end of the probe member to the heart to achieve selective positioning of the electrode or electrodes. A variety of currently available passive and active fixation mechanisms, or that may become available, may be used with the invention. In one embodiment of the invention, the catheter includes a small fixation screw for securing the catheter probe within the heart, wherein the fixation screw is retractable during insertion and removal of the catheter and also functions as a demand pacer stimulating and sensing electrode.

The present invention also provides a system for regulating the beating of a heart. The system includes the catheter, as previously discussed, attached to a pulse generator at the proximal end of the probe. In the preferred embodiment, the pulse generator includes a controller, a defibrillator circuit, and a demand pacer circuit. The controller senses and analyzes the natural electrical charge created by the heart. Depending upon the results of the analysis, the controller informs the demand pacer circuit or defibrillator circuit to discharge either a demand pacer pulse or a defibrillation pulse, respectively. The pulse then travels down the appropriate electrical conductor and is discharged to the heart through the appropriate defibrillation or pacer electrode.

It is therefore an object of the present invention to provide methods and apparatus for regulating the beating of a heart. It is another object of the present invention to provide a single apparatus that can effectively deliver both defibrillator and demand pacer pulses to a heart. Yet another object of the present invention is to provide an apparatus as above that can be inserted in a single surgical procedure. Still another object of the present invention is to provide an apparatus to effectively deliver a defibrillation pulse to the heart without causing electrolysis of the blood. Also, another object of the present invention is to provide an apparatus that effectively delivers a defibrillation pulse, while minimizing the threat of injury to the patient or the heart tissue. It is yet another object of the present invention to provide an apparatus as above that can be selectively positioned in the heart to target a defibrillator or demand pacer pulse so as to deliver the defibrillator or pacer pulse to a precisely defined region of the heart.

Accordingly, the present invention comprises a combination of features and advantages which enable it to substantially advance the technology associated with implantable medical treatment devices. The characteristics and advantages of the present invention described above, as well as additional features and benefits, will be readily apparent to those skilled in the art upon reading the following detailed description and referring to the accompanying drawings.

BRIEF DESCRIPTION OF THE DRAWINGS

For a detailed description of the preferred embodiments of the invention, reference will now be made to the accompanying drawings wherein.

DETAILED DESCRIPTION OF THE PREFERRED EMBODIMENTS

Figure 1:
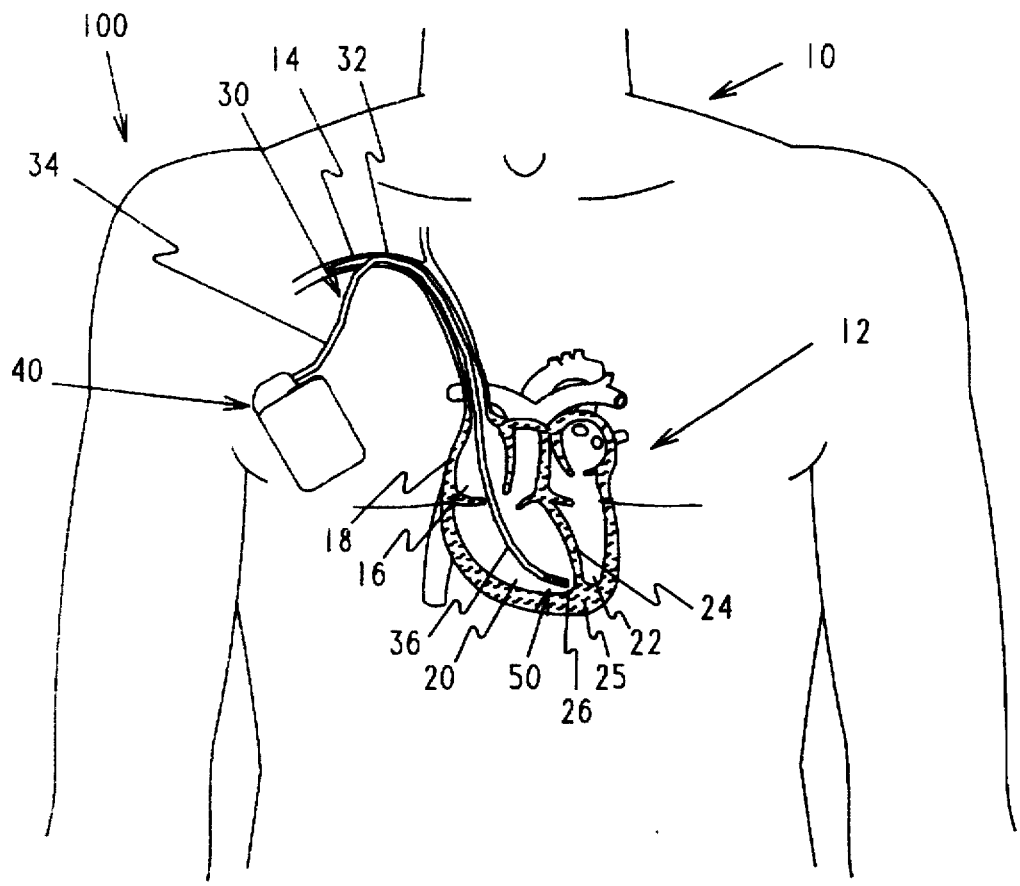
FIG. 1 is a perspective view of a defibrillation and demand pacer catheter of the present invention implanted in the heart of a patient.

The presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic form in the interest of clarity and conciseness.

Referring initially to FIG. 1, a patient 10 is shown having heart 12 with a catheter 30 of the present invention disposed therein. The catheter 30 includes an elongated, flexible, electrically non-conductive probe 32 having a proximal end 34 and a distal end 36. The proximal end 34 of the probe 32 is electrically coupled and attached to a conventional pulse generator 40, while the distal end 36 carries a defibrillation electrode mechanism 50 of the present invention.

The pulse generator 40 may be implanted within or maintained external to the body of the patient 10. The structure, function, and components, such as a power supply and circuitry, of the pulse generator are well known in the art. U.S. Pat. Nos. 4,830,006 and 5,040,534, the entireties of which are incorporated herein by reference, disclose preferred circuitry and components for pulse generator 40 for delivering pacing and defibrillating pulses. The catheter 30 and pulse generator 40 together comprise a catheter system 100 that is capable of controlling the beat of the heart 12 of the patient 10 by delivering to the heart electrical pulses of appropriate energy level and duration.

The catheter 30 extends into the heart 12 through the cephalic or subclavian vein 14 into the right atrium 16 of the heart 12. The right atrium 16 communicates with the right ventricle 20, which is separated from the left ventricle 22 of the heart 12 by the septum 24. As shown in FIG. 1, the distal end 36 of the implanted catheter probe 32 is preferably situated proximate to the right ventricular apex 26.

Depicted in FIGS. 2-5 are enlarged views of the distal end 36 of the catheter probe 32 disposed in the right ventricle 20 of the heart 12. The distal end 36 of the probe 32 carries the defibrillation electrode mechanism 50, which, in the preferred embodiment of FIGS. 1-6, includes first and second defibrillation electrode members 52, 56. Each of the defibrillation electrode members 52, 56 is constructed of a core of highly conductive, non-corrosive metal, such as titanium or platinum, surrounded by a porous coating, as described in U.S. Pat. No. 5,374,287. Other materials known to be effective for use as implantable electrodes may likewise be utilized.

The first defibrillation electrode member 52 has a helical shape and the second defibrillation electrode member 56 has tubular shape. The defibrillation electrode members 52, 56 are electrically coupled to provide a combined optimal electrical transmission surface area for low threshold defibrillation. Accordingly, the electrode members 52, 56 are sized to have a combined surface area large enough to uniformly deliver the effective pulse at energy density levels low enough so as not to burn the heart tissue. It is presently known in the art, for example, that an ideal electrical surface area is between 1.2 centimeters squared and 2.0 centimeters squared, which can be accomplished with the combined surface areas of electrodes 52, 56. Another important consideration that can be accommodated by selectively sizing the first and second electrode members 52, 56 is to minimize longitudinal rigidity for optimal catheter flexibility and ease in insertion and removal.

As shown in FIGS. 2-5, the helical defibrillation electrode member, or helix, 52 is formed with a pre-selected number of turns 52b spaced apart one from the other such that the helix 52 essentially takes the shape of a corkscrew. In the preferred embodiment, the helix 52 is formed with fewer than ten turns 52b for providing an effective defibrillation pulse. Disposed within the center 52c of the helix 52 is an electrically non-conductive core 60, such as polyurethane or silicone rubber. The object of this significant aspect of the present invention is to provide a solid core and smooth outer surface between each of the turns 52b of the helix 52. Since the exposed surface of the combined helix 52 and core 60 has no cavities or sharp protrusions, the potential for forming thrombi, or blood clots thereabouts, is minimized.

Figure 2:
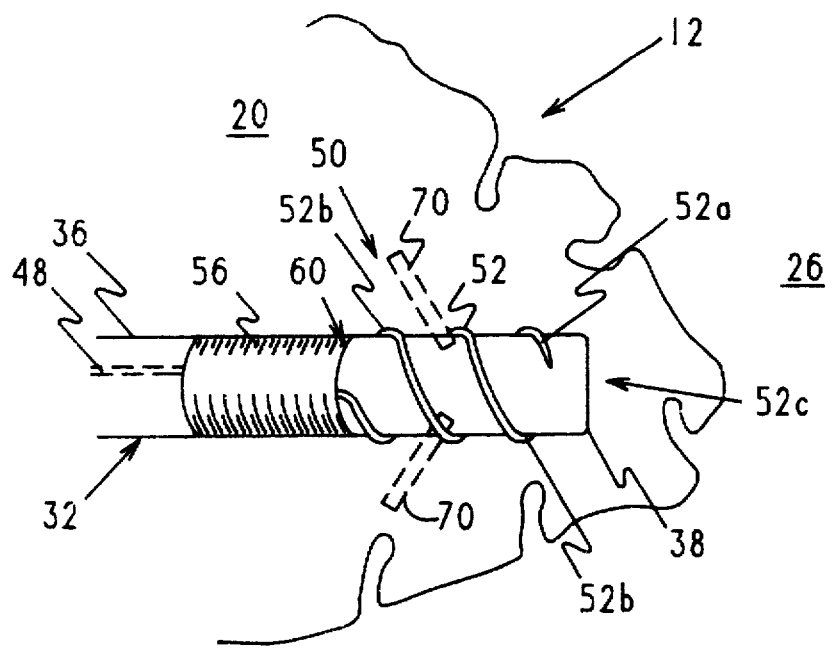
FIG. 2 is an enlarged view of the distal end of the catheter of FIG. 1 having a first embodiment of a defibrillation electrode mechanism of the present invention positioned within the right ventricle of a heart.
Figure 3:
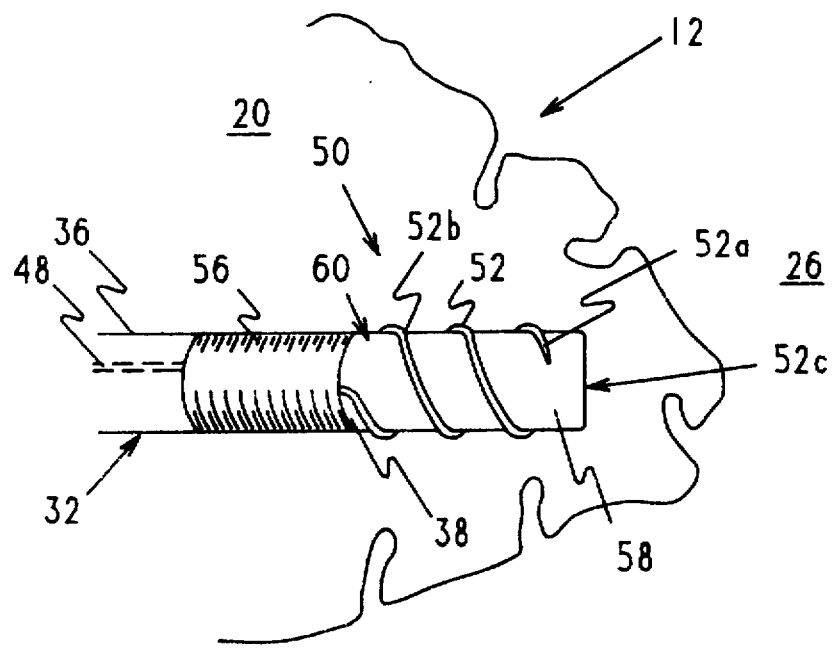
FIG. 3 is an enlarged view of the distal end of the catheter of FIG. 1 having a second embodiment of a defibrillation electrode mechanism of the present invention.

In one preferred embodiment of the defibrillation electrode mechanism 50, as shown in FIG. 2, the helix 52 is disposed about the distal end 36 of the probe 32 adjacent the tip 38 of the probe 32. Thus, the probe 32 itself forms the core 60 of the helix 52. Another preferred embodiment of the defibrillation electrode mechanism 50 is illustrated in FIG. 3, where the helix 52 instead projects longitudinally from the tip 38 of the distal end 36 of the probe 32 and passes over a separate plug member 58 of electrically non-conductive material. In this embodiment, the plug 58 fills the center 52c of the helix 52 and forms its core 60. In both embodiments, in accordance with the present invention, the tip 52a and the turns 52b of the helix 52 are essentially flush against the cylindrical surface of core 60. With the use of the helical defibrillation electrode member 52 of the present invention, the risk of thrombosis or blood clotting that could occur with an open-center helix is minimized. Further, the probe 32 can easily be maneuvered through the cephalic or subclavian vein 14 and the heart 12 during implantation and removal without the risk of the helical electrode member 52 catching upon or tearing the tissue. The defibrillation electrode mechanism 50 thus provides the recognized advantages of a helical shaped electrode without the dangers associated with an open-center helix.

The second defibrillation electrode member 56 is disposed upon the distal end 36 of the probe 32 proximate the first defibrillation electrode member 52, but spaced therefrom by a predetermined distance. The function of this member 56 is to provide additional electrode surface area, and it therefore, can take any shape that is compatible for use on the probe 36 of the catheter 30. Electrode member 56 is illustrated in FIGS. 2-5 as a sleeve 56. Further, the first and second defibrillation electrode members 52, 56 are electrically connected, such as by welding or other conventional connecting techniques or coupling devices.

Figure 4:
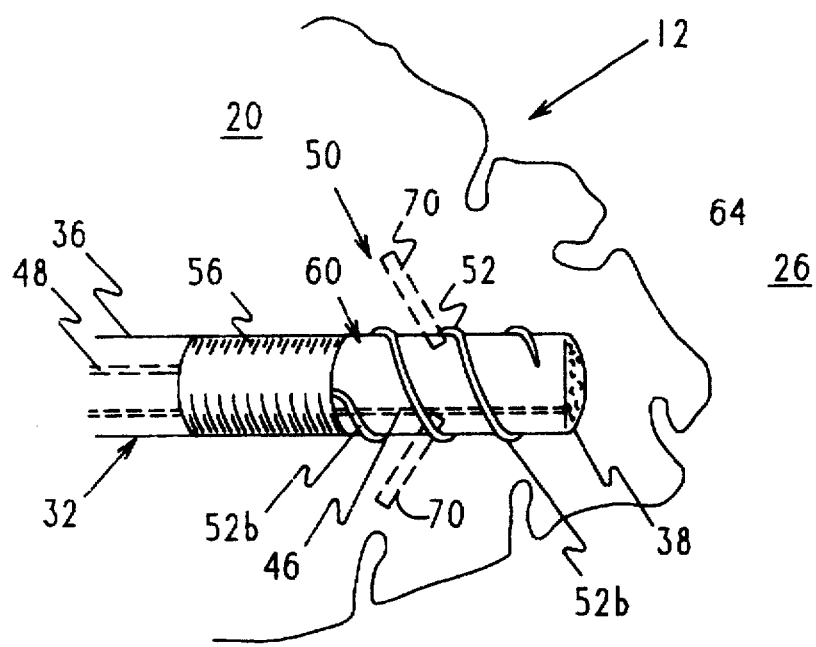
FIG. 4 is an enlarged view of the distal end of the catheter of FIG. 1 having a defibrillation electrode mechanism of the present invention and a demand pacer electrode positioned within the right ventricle of a heart.
Figure 5:
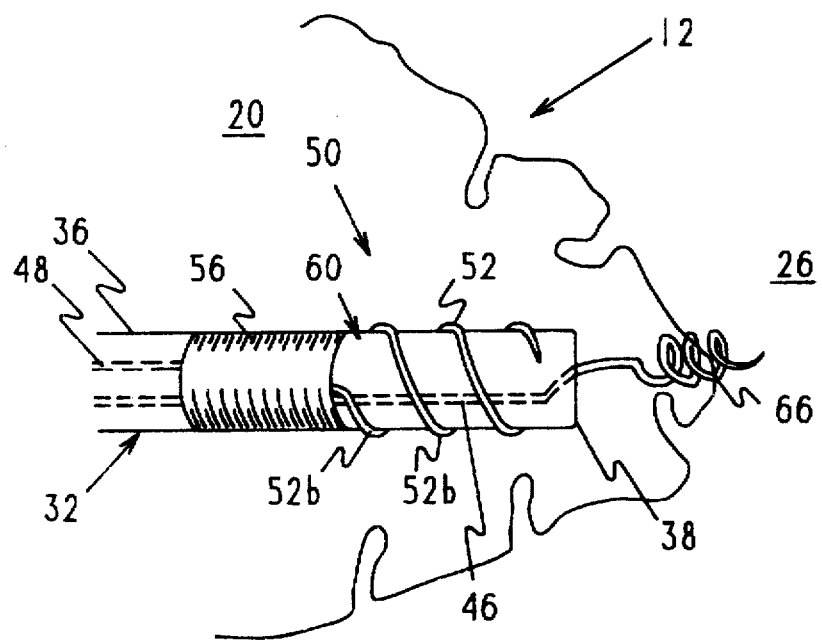
FIG. 5 is an enlarged view of the distal end of the catheter of FIG. 1 having a defibrillation electrode mechanism of the present invention and a combination demand pacer electrode and fixation mechanism anchored to a heart.

The catheter 50 may also be used with a demand pacer, having a conventional demand pacer electrode disposed on the probe a sufficient distance from the first and second defibrillation electrode members 52, 56 to insulate it therefrom. FIG. 4, for example, illustrates a demand pacer electrode 64 disposed on the tip 38 of the distal end 36 of the probe 32. The demand pacer electrode 64 may also serve as a sensor for sensing heart beat and signaling the pacer control components (not shown). In FIG. 5, a demand pacer electrode/sensor combination 66 is shown extending longitudinally from the tip 38 of the distal end 36 of the probe 32. The electrode/sensor 66 is integral with a fixation mechanism, or screw, which will be discussed further below. Any commercially-available demand pacer electrodes or combinations of electrodes, sensors and/or fixation mechanisms that are or may be compatible with the present invention may be utilized.

Figure 6:
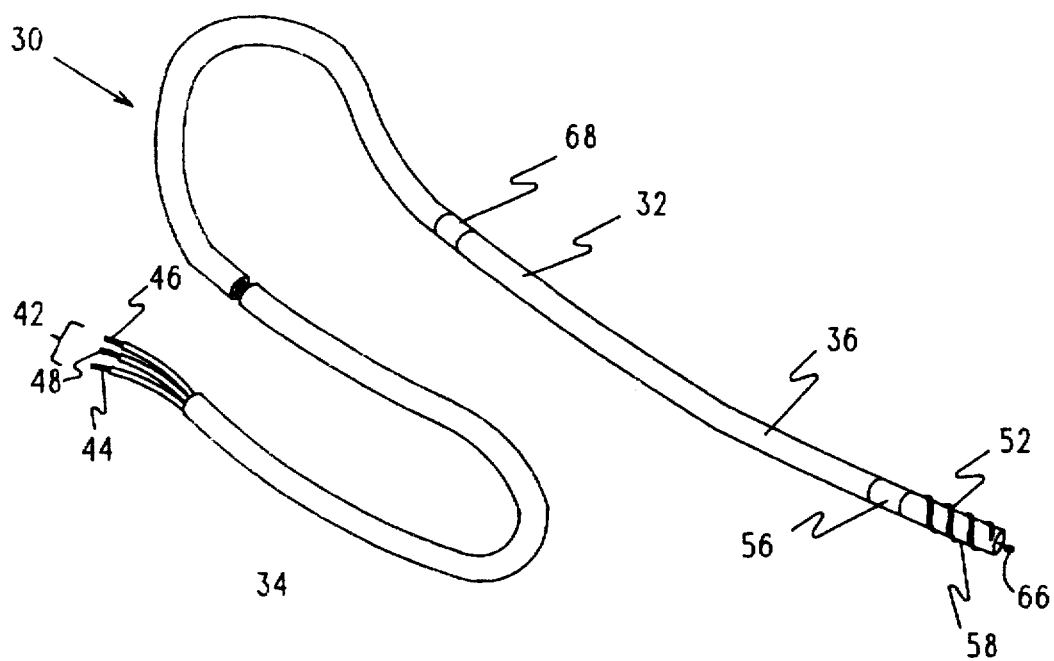
FIG. 6 is a perspective view of a defibrillation and demand pacer catheter system of FIG. 1 including a defibrillation electrode mechanism of the present invention.

In order to use the catheter assembly 100 for defibrillation, or for both defibrillation and demand pacing, a ground electrode is necessary for forming a complete electrical circuit with the other electrodes. Various components can function as a ground electrode. In one configuration, the metal enclosure or "can" of pulse generator 40, may be used as the ground electrode. Alternately, a separate object, such as a patch electrode affixed to the heart, may serve as the ground electrode. Yet another option, as shown in FIG. 6, is a ground electrode 68 disposed on the catheter probe 32 at a location between the proximal end 34 and the distal end 36 of the probe 32. The ground electrode 68 may be constructed and shaped similarly to the second defibrillation electrode member 56, or otherwise as is known in the art.

Electrical signals are delivered to the respective defibrillation and demand pacer electrodes and from the ground electrode through an electrically conductive pathway longitudinally disposed within the probe 32 from the proximal end 34 to the distal end 36 thereof. The embodiment of FIG. 6 includes electrically conductive pathway 42 including a ground conductor 44 electrically coupled with ground electrode 68, demand pacer conductor 46 electrically coupled with the demand pacer electrode 66, and defibrillator conductor 48 electrically coupled with both the first and second defibrillator electrode members 52, 56. The conductors may be any of a variety of commonly available electrical conductors suitable for use in cardiac stimulation devices. All conductor/electrode pairs are insulated from one another so as not to produce an electrical short.

In use, it may be desirable to selectively position the defibrillation and demand pacing electrodes within the right ventricle 20 of the heart 12 for optimum performance. One recognized preferred position of defibrillation and demand pacing electrodes is in the right ventricle 20 of the heart 12 proximate the right ventricular apex 26. FIGS. 1–5 show defibrillation electrodes 52, 56 and FIGS. 4 and 5 show demand pacer electrodes 64, 66 so positioned.

It may also be desirable to anchor the distal end 36 of the probe 32 to the heart 12. To do so, the catheter 30 may include a passive or active fixation mechanism for securing the position of the electrodes within the heart. FIG. 2, for example, illustrates the use of a passive fixation mechanism, or tines, 70 extending from the distal end 36 of the probe 30. After the catheter is positioned within the heart 12, the tines 70 impale themselves or hook into heart tissue, which eventually grows over the tines and secures the distal end 36 of the probe 30 in place. Alternately, an active fixation mechanism, such as a retractable screw may be used. FIG. 5 illustrates a fixation screw 66 extending from the tip 38 of the probe 32 and screwed into the heart tissue. The screw 66 may be a conventional retractable screw or any among a variety of other commercially available configurations known in the art. It is noteworthy that such active fixation mechanisms are small enough to pose little or no risk of damage to the vein or heart during insertion, fixation and removal.

Referring to FIGS. 1–6, to defibrillate the heart 12, a defibrillation pulse is transmitted down defibrillator lead 48 to the defibrillator electrode members 52, 56 for substantially simultaneous discharge into the blood and through the heart 12. The geometry and the proximately of the helix 52 and sleeve 56 allow the delivery of a concentrated, effective pulse without damaging the electrodes or the immediate surrounding heart tissue.

In an alternative method of operation, the catheter 30 can function as a demand pacer, whereby a demand pacer pulse is delivered through the demand lead 46 to the demand pacer electrode 66 (FIGS. 5 and 6). It is well known that the electrical surface area of the demand pacer electrode 66 should be significantly smaller than the electrical surface area of the defibrillator electrode members 52, 56, because the demand pacer pulse has a much smaller current requirement than the defibrillation pulse. Further, it has been recognized that the efficiency of demand pacing is improved by placing the demand pacer electrode 66 in direct contact with the heart tissue for delivering the pulse directly thereto, as shown in FIG. 5.

The catheter 30 can thus be used with the pulse generator 40 as part of a system 100 for regulating the beating of a heart. The pulse generator 40 may include a conventional controller, a defibrillator circuit, and a demand pacer circuit (not shown). The controller senses and analyzes the electrical charge created by the heart. Depending upon the results of the analysis, the controller informs the demand pacer circuit or defibrillator circuit to discharge either a demand pacer pulse or a defibrillation pulse, respectively. The appropriate pulse is then transmitted down the electrically conductive pathway 42 of the catheter and is discharged to the heart through its respective electrode or electrode combination. In all other aspects, the operation of the system 100 can be accomplished in accordance with techniques known in the art.

While preferred embodiments of the present invention have been shown and described, modifications thereof can be made by one skilled in the art without departing from the spirit or teachings of this invention. The embodiments described herein are exemplary only and are not limiting. Many variations and modifications of this system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. An implantable catheter associated with an electrical power source for delivering an electrical pulse to a heart, comprising:

an elongated, flexible electrically nonconductive probe having a proximal end and a distal end, said distal end having a tip, an electrically conductive pathway associated with the power source and disposed within said probe for transmitting and receiving electrical signals through said probe said pathway comprising at least a first electrical conductor, and a defibrillation electrode consisting in combination of
   a helical defibrillation electrode disposed about a plug member of electrically non-conductive material projecting from said tip of said probe, wherein said helical electrode is electrically coupled with said first electrical conductor for transmitting an electrical pulse to the heart, and
   a tubular defibrillation electrode coupled with said distal end of said probe proximate said helical electrode, wherein said tubular electrode is electrically coupled with said helical electrode for transmitting an electrical pulse to the heart.

2. The catheter of claim 1, wherein each of said defibrillation electrodes includes an outer surface having a porous coating.

3. The catheter of claim 1, further comprising a second electrically conductive pathway and a demand pacer electrode disposed on said probe, wherein said demand pacer electrode is electrically coupled with said second electrically conductive pathway for delivering a demand pacing pulse to the heart.

4. The catheter of claim 1, further comprising a fixation mechanism associated with said distal end of said probe for securing said probe within the heart.

5. The catheter of claim 1, wherein said electrically conductive pathway further comprises a second electrical conductor and said catheter further comprises a ground electrode disposed upon said probe between said proximal and distal ends of said probe and electrically coupled with said second electrical conductor.

6. The catheter of claim 1, wherein said plug member of electrically nonconductive material is constructed of polyurethane.

7. The catheter of claim 1, wherein said plug member of electrically nonconductive material is constructed of silicone rubber.

8. The catheter of claim 1, wherein said helical and tubular electrodes have a combined electrical transmission surface area in the range of about 1.2 cm$^2$ to about 2.0 cm$^2$.

9. The catheter of claim 1, wherein said tubular electrode comprises a sleeve.

10. The catheter of claim 1, wherein said helical electrode includes a plurality of adjacent turns and wherein said plurality of turns includes fewer than ten turns.

11. A system for regulating the pulse of the heart of a patient, the system associated with a power source, comprising:

a catheter having
    an elongated, flexible electrically nonconductive probe having a proximal end and a distal end, said distal end having a tip,
    an electrically conductive pathway associated with the power source and disposed within said probe for transmitting and receiving electrical signals through said probe, said pathway comprising at least a first electrical conductor,
    a helical defibrillation electrode disposed about a plug member of electrically non-conductive material projecting from said tip of said probe and electrically coupled with said first electrical conductor,
    a tubular defibrillation electrode disposed upon said distal end of said probe proximate said helical defibrillation electrode, wherein said tubular defibrillation electrode is electrically coupled with said helical defibrillation electrode, a controller capable of sensing and analyzing signals from the heart, and a defibrillator circuit electrically connected with said controller and capable of transmitting an electrical defibrillation pulse to said electrically conductive pathway.

* * * * *